(12) United States Patent
Frangesch et al.

(10) Patent No.: US 6,594,146 B2
(45) Date of Patent: Jul. 15, 2003

(54) DOCKING STATION FOR PATIENT MONITOR OR OTHER ELECTRONIC DEVICE

(75) Inventors: Richard J. Frangesch, Elm Grove, WI (US); Alan E. Clapp, Milwaukee, WI (US); Bart J. Finnel, Cedarburg, WI (US); James M. Gray, Fox Point, WI (US); David L. Schieble, Oconomowoc, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 74 days.

(21) Appl. No.: 09/748,545

(22) Filed: Dec. 26, 2000

(65) Prior Publication Data

US 2002/0082479 A1 Jun. 27, 2002

(51) Int. Cl.[7] ................................................. G06F 1/16
(52) U.S. Cl. ...................................... 361/686; 361/683
(58) Field of Search ................................ 361/686, 683

(56) References Cited

U.S. PATENT DOCUMENTS

| 5,175,671 | A | * | 12/1992 | Sasaki ........................... 361/392 |
| 5,375,604 | A | | 12/1994 | Kelly et al. .................... 128/671 |
| 5,685,314 | A | | 11/1997 | Geheb et al. ................... 128/700 |
| 5,790,375 | A | * | 8/1998 | Lee ................................ 361/686 |
| 5,864,294 | A | * | 1/1999 | Hsu et al. ....................... 340/635 |
| 6,135,801 | A | * | 10/2000 | Helot et al. .................... 439/341 |
| 6,183,417 | B1 | | 2/2001 | Geheb et al. ................... 600/301 |
| 6,185,095 | B1 | * | 2/2001 | Helot et al. .................... 361/686 |
| 6,188,572 | B1 | * | 2/2001 | Liao et al. ..................... 361/686 |

* cited by examiner

*Primary Examiner*—Darren Schuberg
*Assistant Examiner*—Yeah-Hsi Chang
(74) *Attorney, Agent, or Firm*—Ostrager Chong & Flaherty LLP

(57) ABSTRACT

A docking station for a portable electronic device, such as a portable patient monitor of the type used in health care facilities. In particular, the docking station can be installed at a bedside location in a health care facility. The docking station is designed to provide electrical and mechanical connection of AC power and communication devices to the portable electronic device. An intuitive, top-down mounting mechanism locks the electronic device in place without user input. A front facing security lever on the docking station, which can be operated with one hand, provides engagement of electrical connectors and positive locking of the electronic device to the docking station. The docking station combines and provides AC power to the electronic device's AC mains connector, Ethernet signals to communicate with a local area network (LAN), DC power, and asynchronous communication signals to communicate with ancillary devices. A reverse action of the front facing security lever will disconnect the electronic device from these connections and indicate that the electronic device can be safely separated from the docking station. Once the electronic device has been separated from the docking station, the status of the docking station is set to accept the next electronic device.

34 Claims, 12 Drawing Sheets

DOCKING STATION FOR PATIENT MONITOR OR OTHER ELECTRONIC DEVICE

FIELD OF THE INVENTION

This invention generally relates to portable battery-powered electronic devices. In particular, the invention relates to such battery-powered equipment used to monitor patients during transport in a hospital or other patient care setting.

BACKGROUND OF THE INVENTION

When providing medical care to patients, it is frequently necessary to monitor the patient using medical diagnostic instruments. One type of instrument, the patient monitor, is capable of monitoring the patient to acquire electrocardiogram data, cardiac output data, respiration data, pulse oximetry data, blood pressure data, temperature data and other parameter data. In particular, lightweight portable monitors exist which can be moved with the patient, allowing continuous monitoring during patient transport.

To facilitate monitoring at remote locations or during patient transport, modern portable patient monitors are powered by rechargeable batteries. Extended-use batteries, with quick recharge times, help maximize monitor availability. Advanced monitors have a smart battery management system which maximizes battery life, reducing maintenance and replacement. These patient monitors can also be plugged into any conventional electrical power system for use, e.g., at the patient's bedside, before and/or after the patient is transported. At the bedside, advanced patient monitors can be hardwired to a central station via a local area network (LAN) for enhanced patient surveillance efficiency. In addition, the most advanced patient monitors have a built-in wireless option which enables the monitor to go mobile without sacrificing connectivity. Such monitors also support importation of demographic and laboratory data from a hospital information system for increased efficiency.

Portable patient monitors with integral battery power supply are commercially available in a compact, ergonomic package which allows easy handling. Typically such monitors have a drop-tested rugged design which allows them to withstand the punishment of the demanding intra-hospital transport applications. Mounting options make these monitors ideally suited for headboard/footboard, siderail, rollstand and IV pole use. The compact design is achieved in part through the use of flat display panels. The color or monochrome screen accommodates all numerics and multiple waveforms.

In addition to displaying waveforms and numerics representing the data being acquired, advanced patient monitors have a central processing system which stores and analyzes the acquired data. In particular, the central processing system is programmed with algorithms for analyzing the acquired data. The central processing system controls the transfer of data to the display panel for display and to the LAN via either a hardwired or wireless connection.

As used at a bedside location, a portable patient monitor can be attached to fixed mounting means, such as a slide rail device (commonly called GCX), and connected to an AC power source and to data communications connectors. An assortment of cables are required to provide AC power, Ethernet support and auxiliary data communications to the patient monitor. To connect and disconnect cables while attaching and detaching the patient monitor from its mounting is time consuming and cumbersome. There is a need for an apparatus which would simplify and facilitate the procedure for connecting a portable patient monitor to an AC power source and to data communications systems at a bedside location at a health care facility.

SUMMARY OF THE INVENTION

The present invention is directed to a docking station for a portable electronic device, such as a portable patient monitor of the type used in health care facilities. In particular, the docking station can be installed at a bedside location or treatment location, such as X-ray, etc., in a health care facility. The docking station is designed to provide electrical and mechanical connection of AC power and communication devices to the portable electronic device. An intuitive, top-down mounting mechanism locks the electronic device in place without user input. A front facing security lever on the docking station, which can be operated with one hand, provides engagement of electrical connectors and positive locking of the electronic device to the docking station. The docking station combines and provides AC power to the patient monitor's AC mains connector, Ethernet signals to communicate with a local area network (LAN), DC power, and asynchronous communication signals to communicate with auxiliary devices. A reverse action of the front facing security lever will disconnect the electronic device from these connections and indicate that the electronic device can be safely separated from the docking station. Once the electronic device has been separated from the docking station, the status of the docking station is set to accept the next electronic device.

In accordance with the preferred embodiment disclosed herein, the docking station is used as a pass-through device. However, it will be appreciated that the docking station could also be provided with enhanced capabilities.

A docking station in accordance with one preferred embodiment comprises: a housing for supporting a patient monitor in a predetermined position; a release mechanism which is activated by the weight of the patient monitor; and a spring-loaded clamping mechanism held in a non-clamping state prior to the release mechanism being activated and changed to a clamping state under the influence of spring loading in response to activation of the release mechanism. The patient monitor is clamped to the docking station when the clamping mechanism is in its clamping state. The release mechanism preferably comprises a plunger which penetrates an opening in the housing and which is displaced downward and further into the housing as the patient monitor is lowered into the aforementioned predetermined position.

A docking station in accordance with another preferred embodiment of the invention comprises: a housing for supporting a patient monitor in a predetermined position; a platform which is vertically displaceable inside the housing; an electrical connector mounted to the platform; and a lever assembly coupled to the platform and comprising a user-operable device protruding external to the housing. The platform is displaced upward in response to a predetermined movement of the user-operable device, whereby the electrical connector is mated with an electrical connector of the patient monitor. The user-operable device preferably comprises a lever which is pivotable relative to said housing. Preferably the connector platform carries an AC power connector and data communications connectors.

The most preferred embodiment of the invention comprises both a spring-loaded actuator for clamping an electronic device to a docking station and a user-operable lever for connecting the electronic device to AC power and data communications connectors in one motion.

The invention further encompasses a method of using a portable electronic device, comprising the steps of: transporting an electronic device to a site where a docking station is situated; placing the electronic device on the docking station in a predetermined positional relationship; and manipulating an actuator on the docking station which causes the electronic device to be connected to an electrical power source via the docking station.

Other aspects of the invention are disclosed and claimed below.

DETAILED DESCRIPTION OF THE PREFERRED EMBODIMENTS

Figure 1:
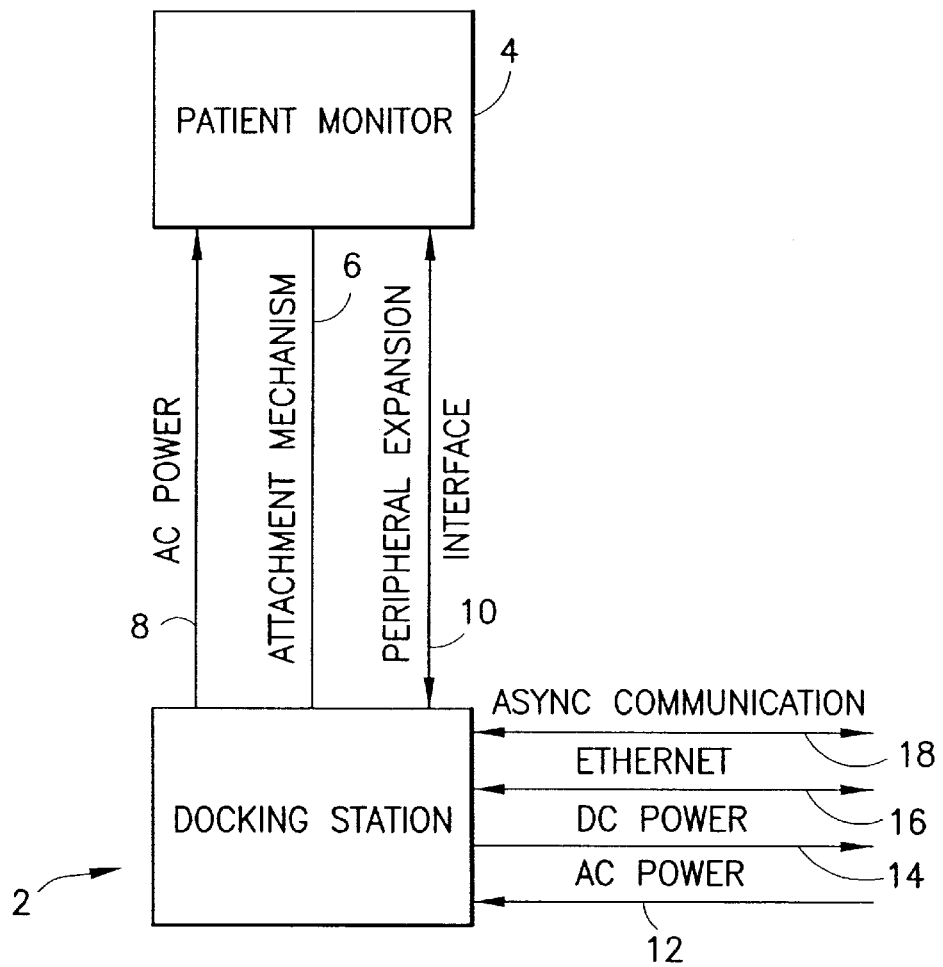
FIG. 1 is a block diagram generally showing a patient monitor mechanically and electrically coupled to a docking station.

FIG. 1 generally depicts the desired connections between a docking station 2 and a patient monitor 4. The docking station 2 provides mechanical and electrical connection of AC power and communications devices to the patient monitor 4. The physical attachment mechanism is indicated by line 6; the AC power connection is indicated by arrow 8; and a peripheral expansion interface 10 is indicated by bidirectional arrow 10 in FIG. 1. The peripheral expansion interface 10 includes DC power, one asynchronous communication channel and an Ethernet communication channel.

An intuitive, top-down mounting mechanism (described in detail below) locks the monitor 4 in place without user input. A front facing security lever (item 20 in FIG. 2) on the docking station 2, which is operated with one hand, provides engagement of electrical connectors and positive locking of the patient monitor 4 to the docking station 2. This connector combines and provides AC power (arrow 12) to the monitor's AC mains connector; Ethernet signals (bi-directional arrow 16) to communicate with a local area network (LAN); DC power (arrow 14); and asynchronous communication signals (bi-directional arrow 18) to communicate with ancillary devices. A reverse action of the front facing security lever will disconnect the monitor 4 from these connections and indicate that the monitor 4 can be safely separated from the docking station 2. Once the monitor 4 has been separated from the docking station 2, the status of the device is set to accept the next patient monitor.

Figure 2:
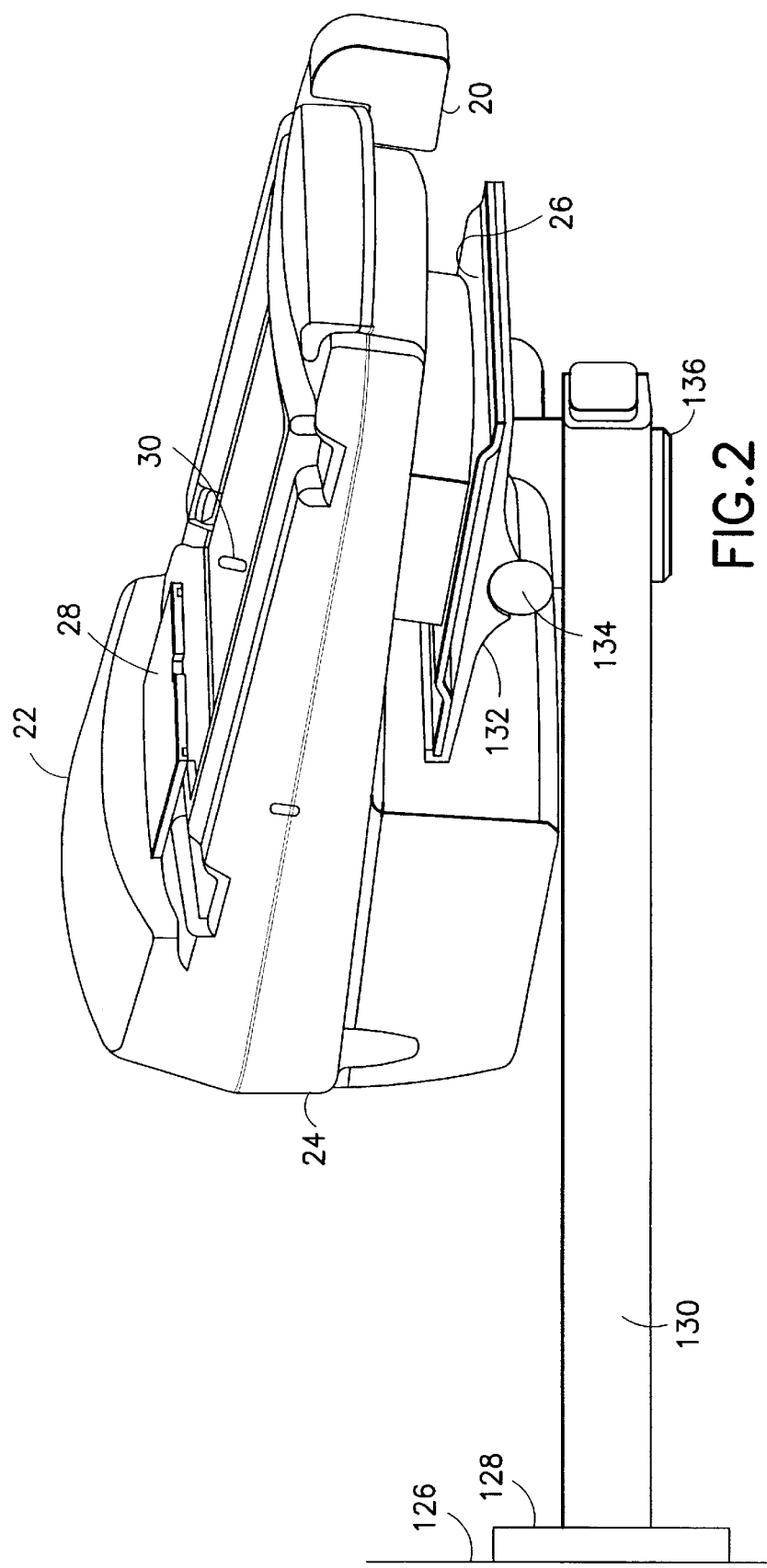
FIG. 2 is a drawing showing a docking station in accordance with the preferred embodiment of the invention, mounted on the end of a wall-supported mounting arm.

FIG. 2 depicts one exemplary arrangement for supporting a docking station on a wall 100 by means of a support arm 104 secured to the wall 100 by means of a mounting plate 102. The support structure further comprises a base 106 which can be swiveled on a horizontal pivot rod 108, the latter in turn being attached to a pivotable post 110. The docking station 2 comprises a top housing 22 and a bottom housing 24. The bottom housing 24 is connected to a mounting plate 26, which is in turn fastened to the support base 106. Thus the docking station has the same degrees of freedom of movement that base 106 has.

The top and bottom housings are configured to form a curved horizontal slot which is penetrated by a user lever 20. As will be explained in detail below, the user lever 20 is connected to a pivotable main lever housed inside the docking station which actuates the electrical connection and physical locking of the patient monitor to the docking station. The user lever swings from right to left in two stages. In the first stage, the user lever is swung about one-half of the way from right to left in response to triggering of a spring action; in the second stage, the user lever is swung all the way to the left by user manipulation. The spring action is triggered by depression of the plunger pin 30 due to the weight of the monitor placed atop the docking station. During the first stage of lever motion, the patient monitor is clamped in place; during the second stage, the patient monitor is electrically connected and positively locked to the docking station. The user lever is swung from left to right to release the patient monitor. The spring-loaded plunger pin 30 is cocked by lifting the monitor up from the docking station.

Figure 3:
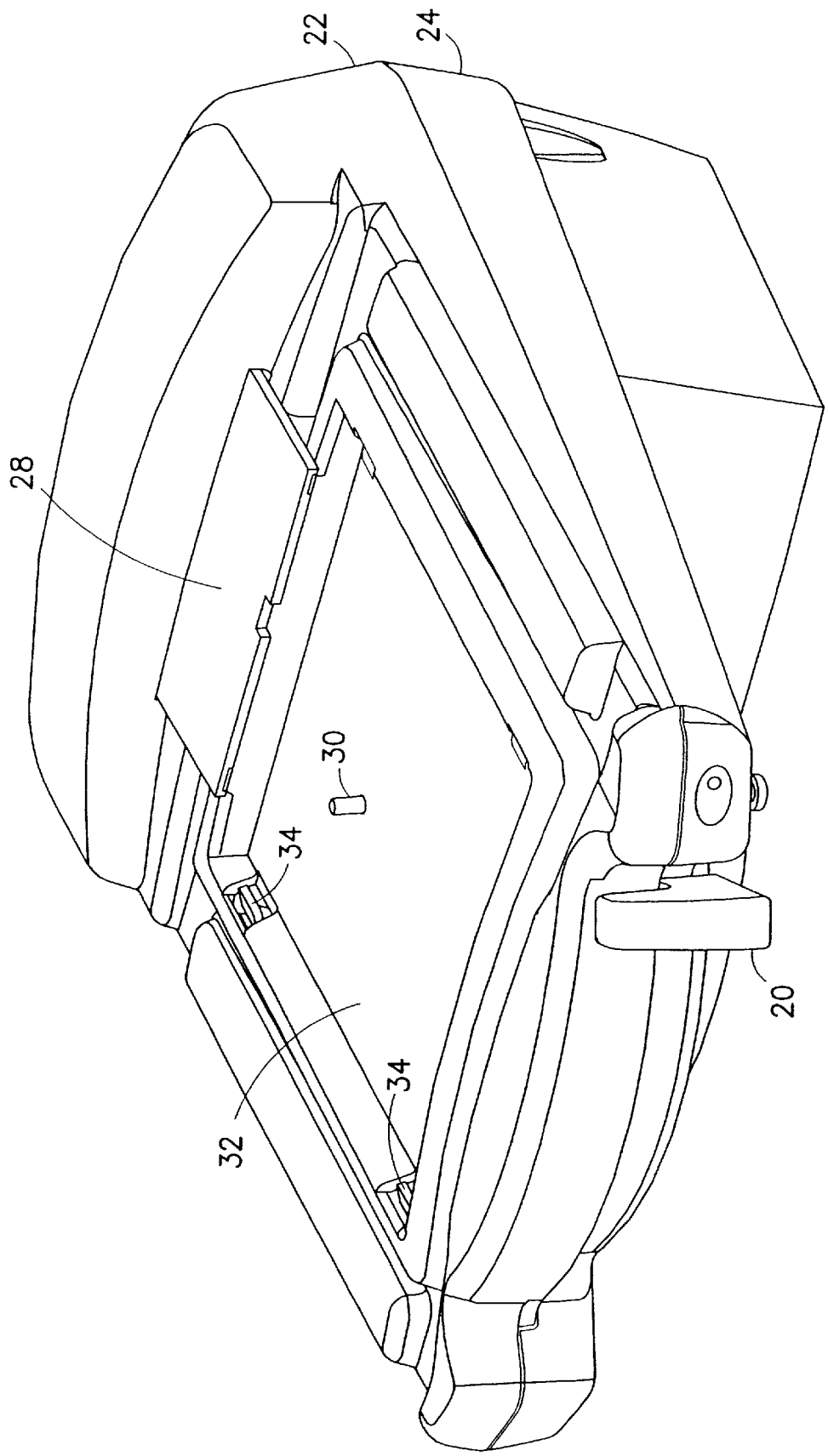
FIG. 3 is a drawing showing a docking station in accordance with the preferred embodiment of the invention in a cocked state, ready to receive a patient monitor.
Figure 4:
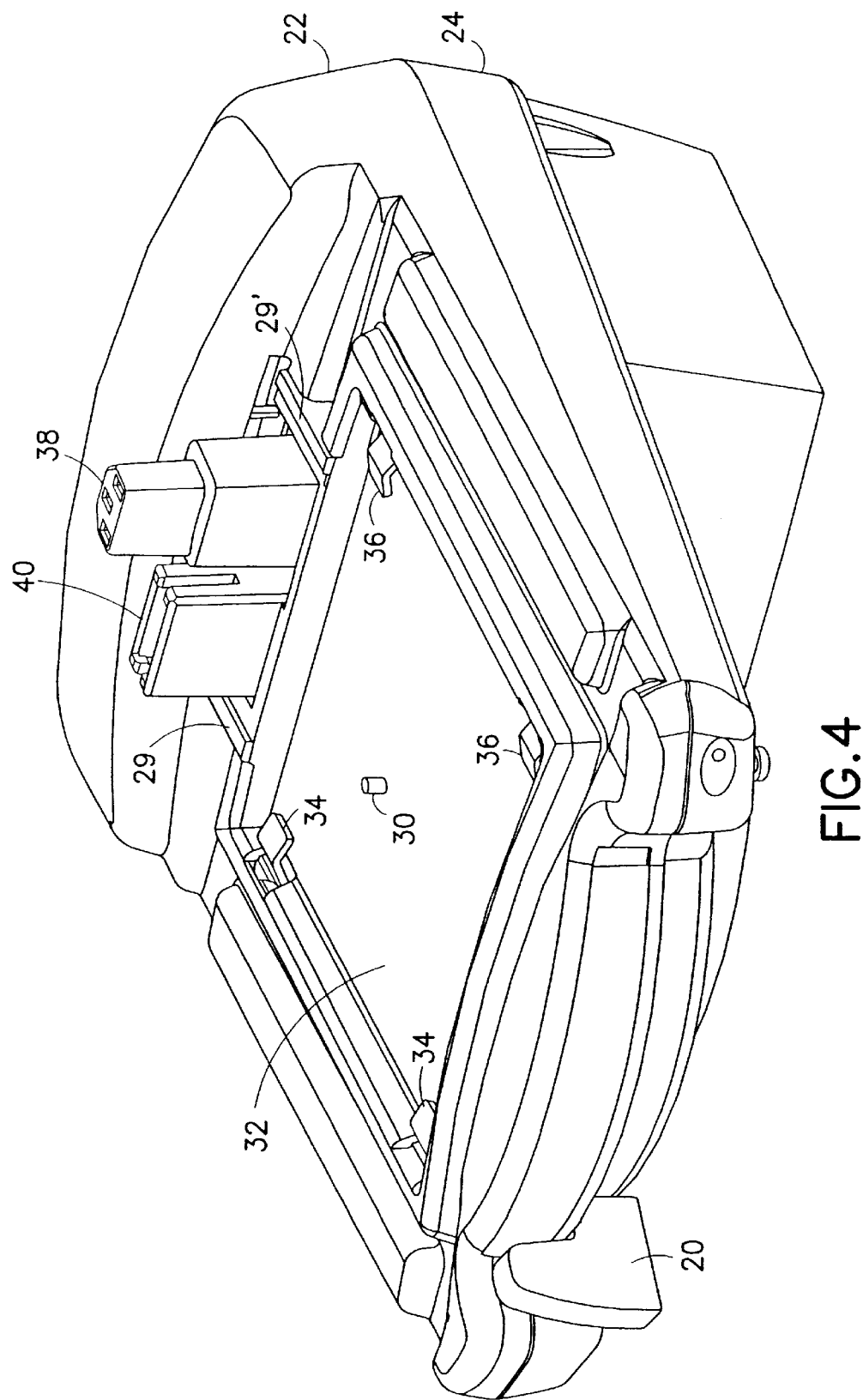
FIG. 4 is a drawing showing a docking station in accordance with the preferred embodiment of the invention when a patient monitor (not shown) is docked.

In FIG. 3, the docking station 2 is shown ready to accept a monitor, with the connector door 28 shown in its closed position. The power and communications connectors are located in a cavity under the connector door. The user lever 20 is in its rightmost position. FIG. 4 shows the docking station after a monitor has been placed in the recessed seat 32 formed in the top housing 22 of the docking station and after the user lever 20 has been pushed to its leftmost position. The connector door has been slid to its open position, and the AC power connector 38 and the communications 40 have been raised into engagement with mating connectors inside the patient monitor (not shown).

The plunger pin 30 is located approximately in the center of the seat 32 and is displaceable along its axis between up and down positions. Although not shown in FIGS. 3 and 4, the plunger pin 30 is supported by a compression spring which sits in a cylindrical recess having a closed bottom. The compression spring provides an upward bias which urges the plunger pin toward the fully up position shown in FIG. 3. Under the weight of the monitor, the spring bias is overcome and the plunger pin is pushed downward to the position shown in FIG. 4.

Although not shown in FIGS. 3 and 4, the user lever 20 is spring biased to swing from right to a position one-half to the left. This spring action is triggered by depression of the plunger pin 30. The operator then manually moves the user lever 20 to its leftmost position.

During transit of the user lever from its rightmost position to its leftmost position, two pairs of clamping fingers 34 and 36, protruding through openings on opposing sides of the monitor seat 32, are moved toward each other and into corresponding recesses (not shown) formed in the patient monitor. Only clamping fingers 34 of the first pair are visible in FIG. 3. The clamping fingers 34 are shown in the retracted position in FIG. 3, allowing the monitor (not shown) to be placed onto the docking station. FIG. 4 shows the clamping fingers 34 and 36 in their fully extended positions, in which the patient monitor is positively locked to the docking station.

Figure 5:
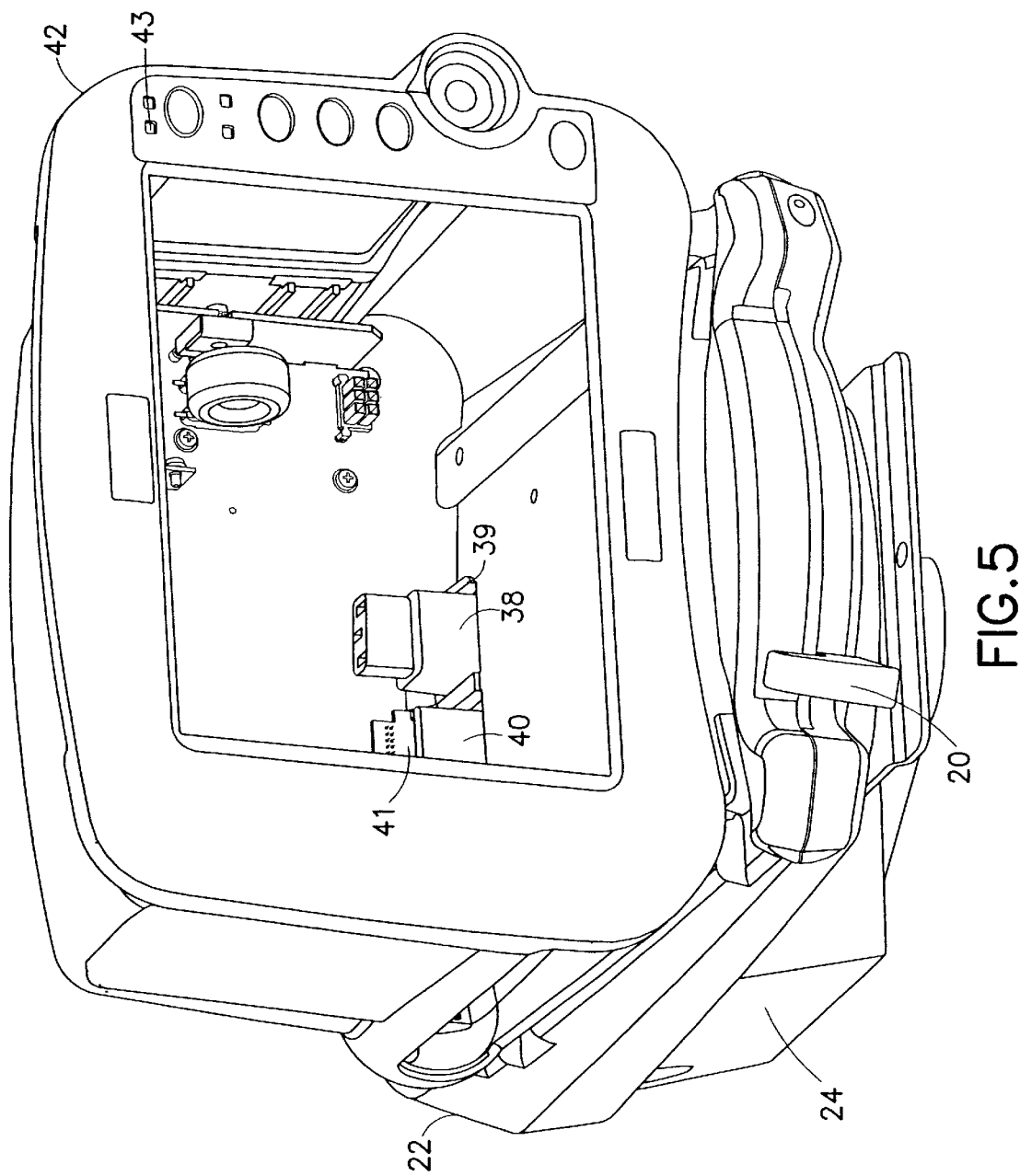
FIG. 5 is a drawing showing a patient monitor docked to a docking station in accordance with the preferred embodiment of the invention. The patient monitor is shown with the display screen and most internal components removed.

During transit of the user lever 20 along the first one-half of its stroke, the connector door 28 is opened. During transit of the user lever 20 along the final one-half of its stroke, the AC power connector 38 and the communications connector 40 are raised to the fully up position shown in FIG. 4. During this upward movement, the connectors 38 and 40 penetrate an opening 39 in the bottom of the patient monitor housing 42, shown in FIG. 5 with the display screen and most internal components removed. Item 41 indicates part of the printed circuit board inside the patient monitor. An edge of the board interacts with a multiplicity of spring finger contacts inside the recess of the communications connector 40. When the patient monitor becomes coupled to the AC power connector 38 of the docking station, this state will be indicated by activation of a light-emitting diode (LED) 43 which is visible on the patient monitor exterior.

The above-described mechanical movements are accomplished via a lever assembly, which will now be described with reference to FIGS. 6–9. In FIGS. 6–9, the docking station is shown with its top housing removed to illustrate the mechanical components inside. It should be understood, however, that the lever mounting bracket 52 (best seen in FIG. 8) is fastened to the top housing (not shown). A main lever 44 is pivotably mounted to the lever mounting bracket 52 by means of a main shoulder pivot bolt 46. The main lever 44 is connected to the user lever 20, as best seen in FIG. 7. As the user lever 20 is moved from its rightmost to its leftmost position, the main lever rotates through an angle of about 60 degrees. The lever mounting bracket 52 has a circular opening 53 (shown in FIG. 9) through which a plunger pin housing protrudes. The plunger pin housing is integrally formed as part of the bottom housing and comprises a circular cylindrical tube which is closed at the bottom and open at the top. A compression spring is seated inside the tube, with the plunger pin being slidably arranged inside the top with the compression spring underneath.

Figure 8:
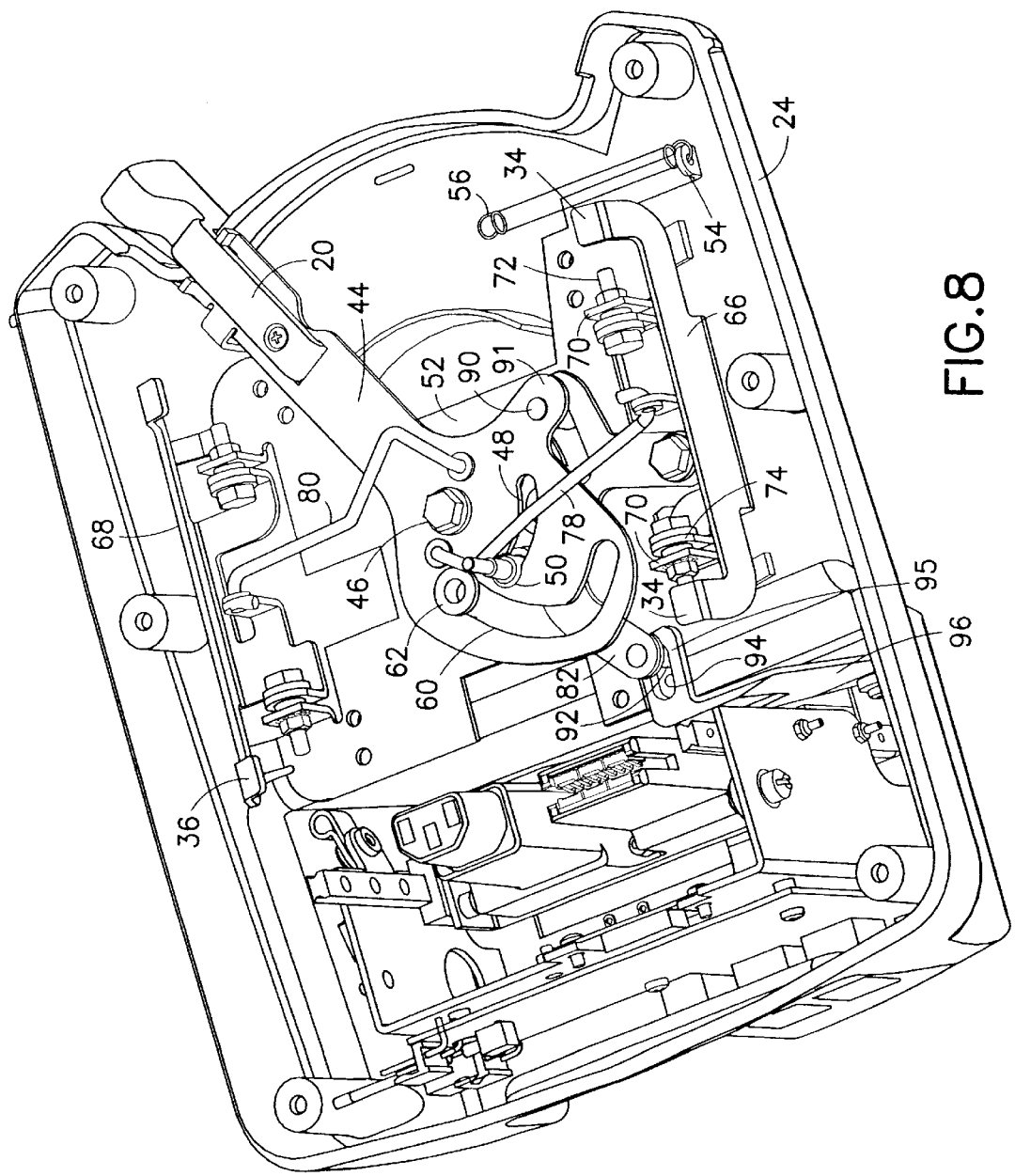
FIG. 8 is a drawing showing another view of the internal components of the docking station of FIG. 6, with the connector door now removed.

The main lever 44 comprises an arcuate slot 48 having a keyhole 50 at one end. The arcuate slot 48 has a radius of curvature centered at the axis of the shoulder pivot bolt 46. The plunger pin 30 protrudes through the keyhole 50, as best seen in FIG. 8. The plunger pin 30 preferably comprising three section of increasing diameter. The topmost section of the plunger pin 30 is a circular cylinder having a small diameter which allows the topmost pin section to protrude through a small circular opening in the monitor seat 32, as shown in FIG. 3. The bottommost section of the plunger pin 30 is a circular cylinder having a large diameter which is greater than the width of the arcuate slot 48 and slightly less than the diameter of the keyhole 50. Finally, the middle section of the plunger pin 30 is a circular cylinder having a diameter slightly smaller than the width of the arcuate slot 48.

Figure 6:
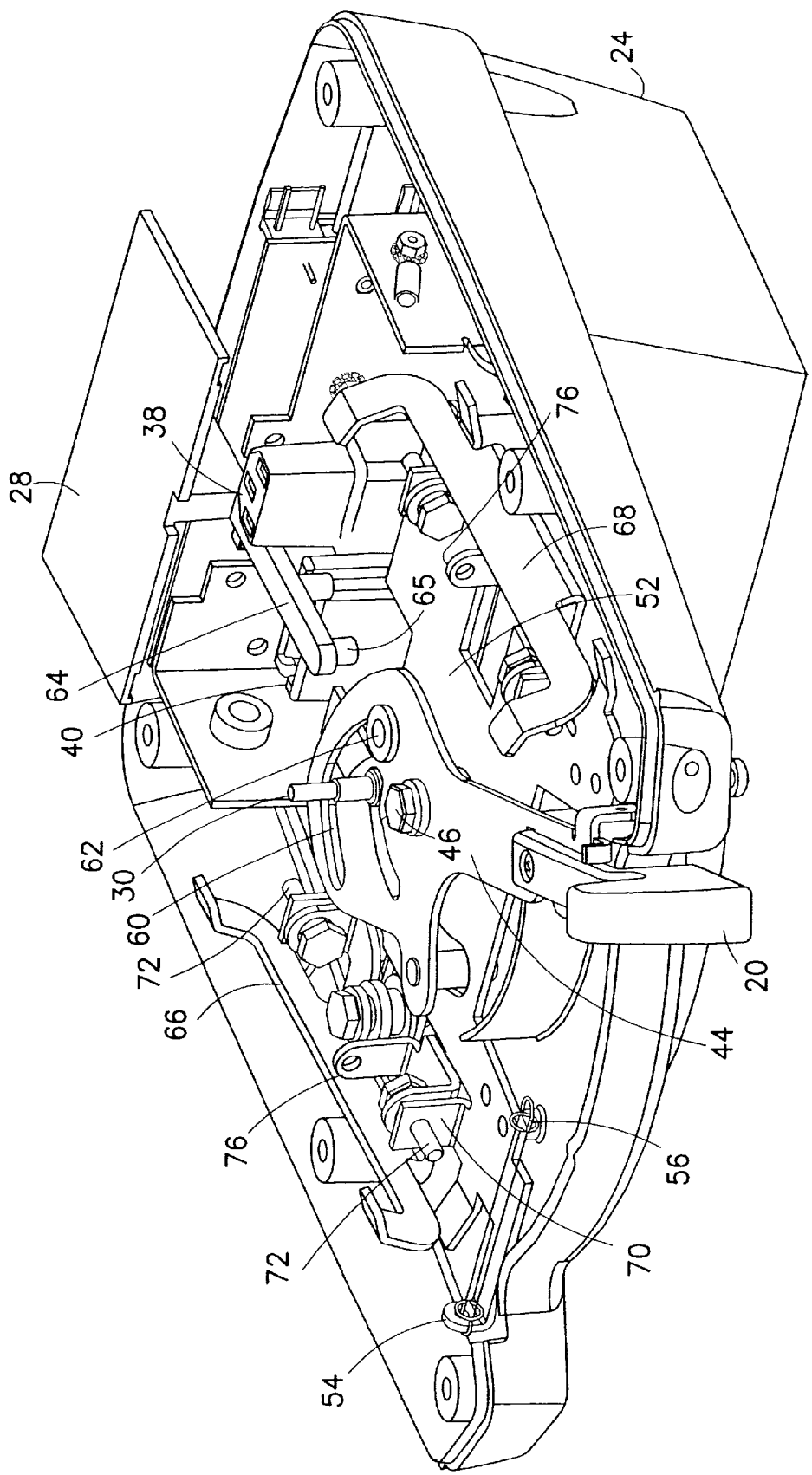
FIG. 6 is a drawing showing a docking station in accordance with the preferred embodiment of the invention with the top housing removed to reveal the internal mechanical and electrical components. The docking station is shown in its cocked state, except that the connector door is shown in its open position and uncoupled from the main lever assembly.
Figure 7:
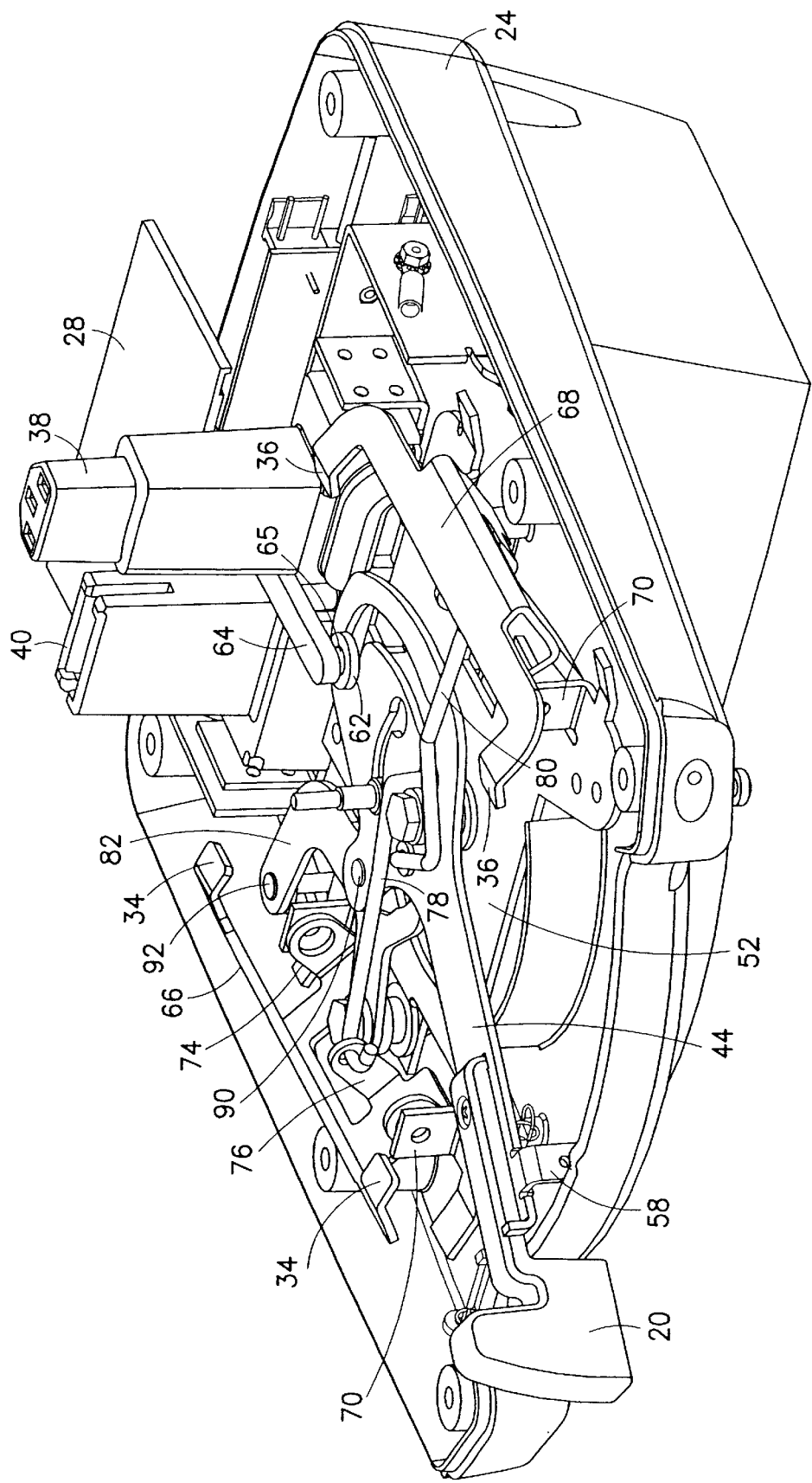
FIG. 7 is a drawing showing the docking station of FIG. 6 after the user lever has been fully actuated.

The plunger pin 30 can be in its fully up position (as seen in FIGS. 6 and 8) only when the large-diameter section of the plunger pin engages the keyhole 50. In this position, the main lever 44 is locked in position and cannot rotate. When the plunger pin 30 is depressed, as previously described, the large-diameter portion of the plunger pin is pushed out of the keyhole 50 and replaced by the intermediate-diameter portion. Since the intermediate diameter portion of the plunger pin is sized to fit in the arcuate slot 48, the plunger pin 30 no longer blocks clockwise pivoting of the main lever 44. When the plunger pin 30 is released from the keyhole 50, the spring-loaded main lever 44 pivots, during which motion the plunger pin 30 follows the arcuate slot 48.

As seen in FIG. 8, the lever mounting bracket 52 comprises a bracket 54 which anchors an extension spring 56. Although the extension spring 56 is only partially depicted and is shown not attached at the end remote from the anchor, it should be understood that the remote end of the extension spring 56 is attached to a tab 58 (see FIG. 7) which is integrally formed as part of the main lever 44. To maximize the torque applied to the main lever by the extension spring 56, the tab 58 is located on the main lever 44 at a point furthest away from the shoulder pivot bolt 46. The extension spring 56 urges the main lever 44 to swing clockwise from the starting angular position corresponding to the rightmost position of the user lever 20. However, that clockwise rotation of the main lever 44 cannot occur until the intermediate-diameter portion of the plunger pin 30 intersects the keyhole 50. Because the intermediate-diameter portion of the plunger pin 30 can enter the arcuate slot 48, the main lever 44 is free to rotate clockwise, at the urging of the extension spring 56, until the plunger pin reaches the termination of the arcuate slot 48.

As seen in FIG. 8, the main lever has a camming slot 60 which accepts and interacts with a bushing 62. The bushing 62 in turn accepts a pin 65 depending from one end of a cam follower 64. The other end of the cam follower 64 is connected to and supports the connector cover 28, as best seen in FIG. 6. For the purpose of illustration, the cam follower 64 is shown uncoupled from the bushing 62. FIG. 7 shows the cam follower 64 coupled to the bushing 62. As seen in FIG. 4, the connector door 28 slides on a pair of parallel rails 29 and 29'. As the main lever 44 pivots under the urging of the extension spring 56, the camming slot 60 cams the cam follower 64 rearward, causing the connector door 28 to slide open, as shown in FIGS. 4 and 7. After the camming action has been completed, the camming slot 60 changes direction, as seen in FIG. 8, terminating in an arcuate section which has a radius of curvature centered at the axis of the shoulder pivot bolt 46. When the bushing 62 is riding in this section of slot 60, no further rearward displacement of the connector door 28 occurs as the main lever 44 is pivoted by the operator along the final one-third of its stroke.

During the above-described rotation of the main lever 44, a pair of lever clamps are moved into engagement with the patient monitor, locking it in place. FIG. 6 shows the positions of left and right lever clamps 66 and 68 when the user lever 20 is in its rightmost position. Each lever clamp 66 and 68 is pivotably mounted to a respective pair of tabs 70 integrally formed as part of the lever mounting bracket 52. FIG. 6 shows the shoulder pivot bolts 72 which couple the left lever clamp 66 to a pair of tabs 70. FIG. 7 shows the lever clamps 66 and 68 when the user lever 20 is in the left most position. The shoulder pivot bolts have been removed in FIG. 7 to better show the shape of the pivot brackets 74, which are integrally formed as part of the lever clamps.

As shown in FIG. 7, each lever clamp comprises a hook bracket 76 for coupling to one end of respective lever rods 78 and 80, the other ends of which are coupled to the main lever 44. The lever rods are not shown in FIG. 6.

As best seen in FIG. 8, the left lever clamp 66 is coupled to the main lever 44 by the left lever rod 78, while the right lever clamp 68 is coupled to the main lever 44 by the right lever rod 80. Each lever rod has a hook-shaped end which hooks to the respective hook brackets 76 of the lever clamps. The other ends of the left and right lever rods 78 and 80 are fitted in respective holes in the main lever located on opposing sides of and adjacent to the shoulder pivot bolt 46. During rotation of the main lever 44, the left and right clamp levers 66 and 68 are pulled toward each other by the left and right lever rods 78 and 80, respectively. FIG. 7 shows the lever clamps 66 and 68 in the closed positions whereat the fingers 34 and 36 of the clamp levers 66 and 68 respectively are fully extended, as shown in FIG. 4, thereby positively locking the patient monitor to the docking station.

Figure 9:
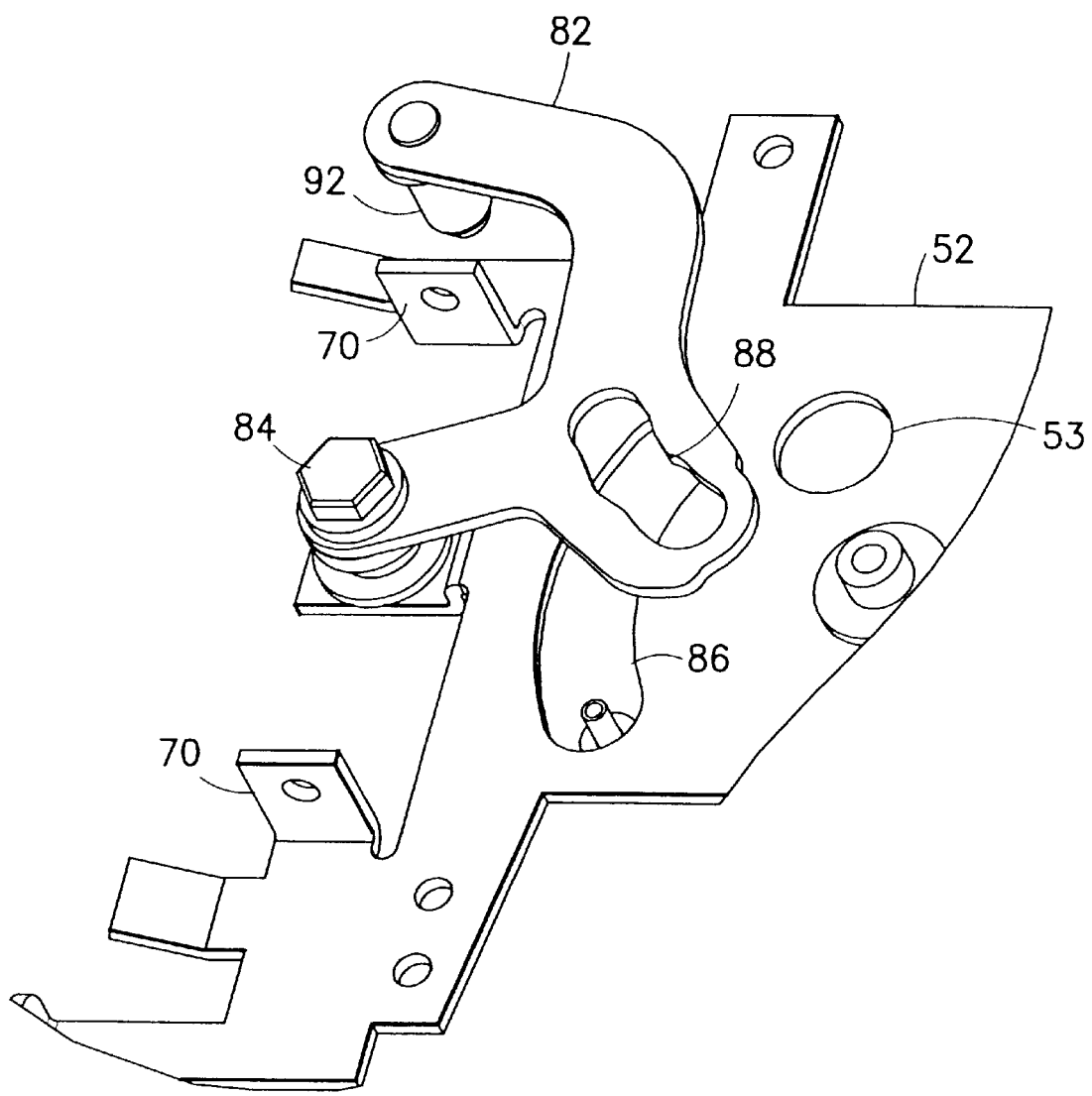
FIG. 9 is a drawing showing an intermediate lever pivotably mounted to a lever mounting bracket in accordance with the preferred embodiment of the invention.

In accordance with the preferred embodiment of the invention, an intermediate lever 82 is also pivotably mounted to the lever mounting bracket 52. The intermediate lever 82 is situated between the main lever 44 and the lever mounting bracket 52. As best seen in FIG. 9, the intermediate lever 82 is rotatable on a shoulder pivot bolt 84 which is affixed to the lever mounting bracket 52. The lever mounting bracket 52 has an arcuate slot 86 having a radius of curvature centered at the axis of the shoulder pivot bolt 46. The intermediate lever 82 has a shorter arcuate slot 88 which has the same radius of curvature as that of slot 86. Initially (i.e., when the user lever is in its rightmost position), the arcuate slot 88 of the intermediate lever 82 overlies the arcuate slot 86 of the lever mounting bracket 52.

Referring to FIG. 8 again, the slots 86 and 88 are penetrated by a pin 90 extending downward from an extension 91 of the main lever 44. As the main lever 44 rotates during transit of the user lever from its rightmost position to a position one-half along the full stroke of the user lever, the pin 90 travels in the arcuate slots 86 and 88 without acting on the pivotable intermediate lever 82. In other words, the pin 90 has an arc of lost motion until it reaches the end of the arcuate slot 88 in the intermediate lever 82. At that point, further rotation of the main lever 44 in the clockwise direction causes the intermediate lever 82 to rotate in a counterclockwise direction about a vertical axis.

As seen in FIG. 9, the intermediate lever 82 has its own pin 92 which lies at a predetermined distance from the shoulder pivot bolt 84. As seen in FIG. 8, the pin 92 is inserted in an oblong slot 94 formed in a tab 95 of an L-shaped connector lever 96. The connector lever 96 is pivotable about a pivot pin having a horizontal axis. The coupling of pin 92 in slot 94 converts the pivoting of intermediate lever 82 about a vertical pivot axis into pivoting of connector lever 96 about a horizontal pivot axis. This pivoting of the connector lever 96 occurs while the user lever is being moved from its halfway position to its leftmost position, as previously described.

Figure 10:
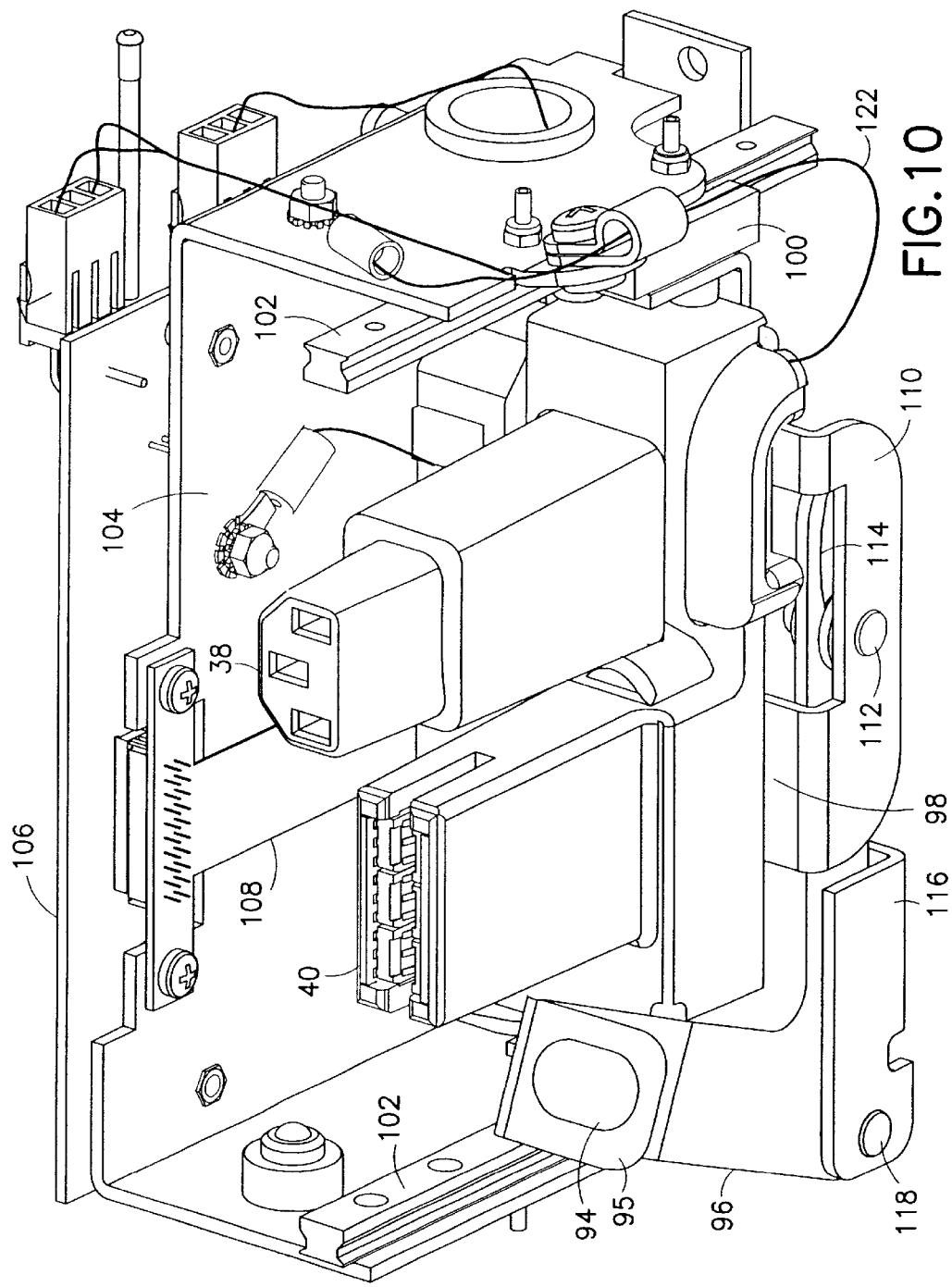
FIGS. 10 and 11 are drawings showing the electrical connector subassembly of the docking station in accordance with the preferred embodiment of the invention, viewed from above and below, respectively. The connectors are shown in the retracted state, i.e., not coupled to the patient monitor.
Figure 11:
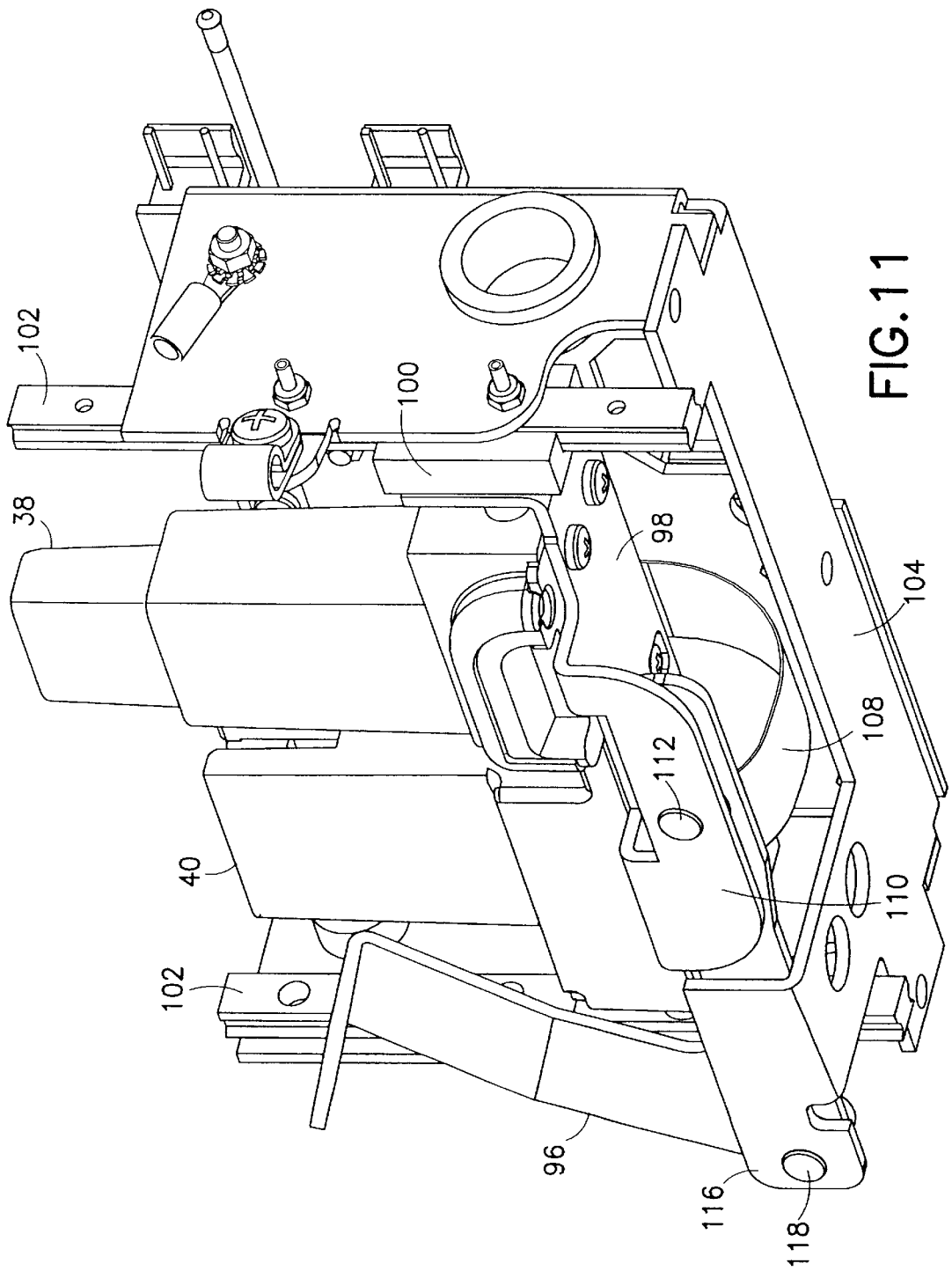
Figure 12:
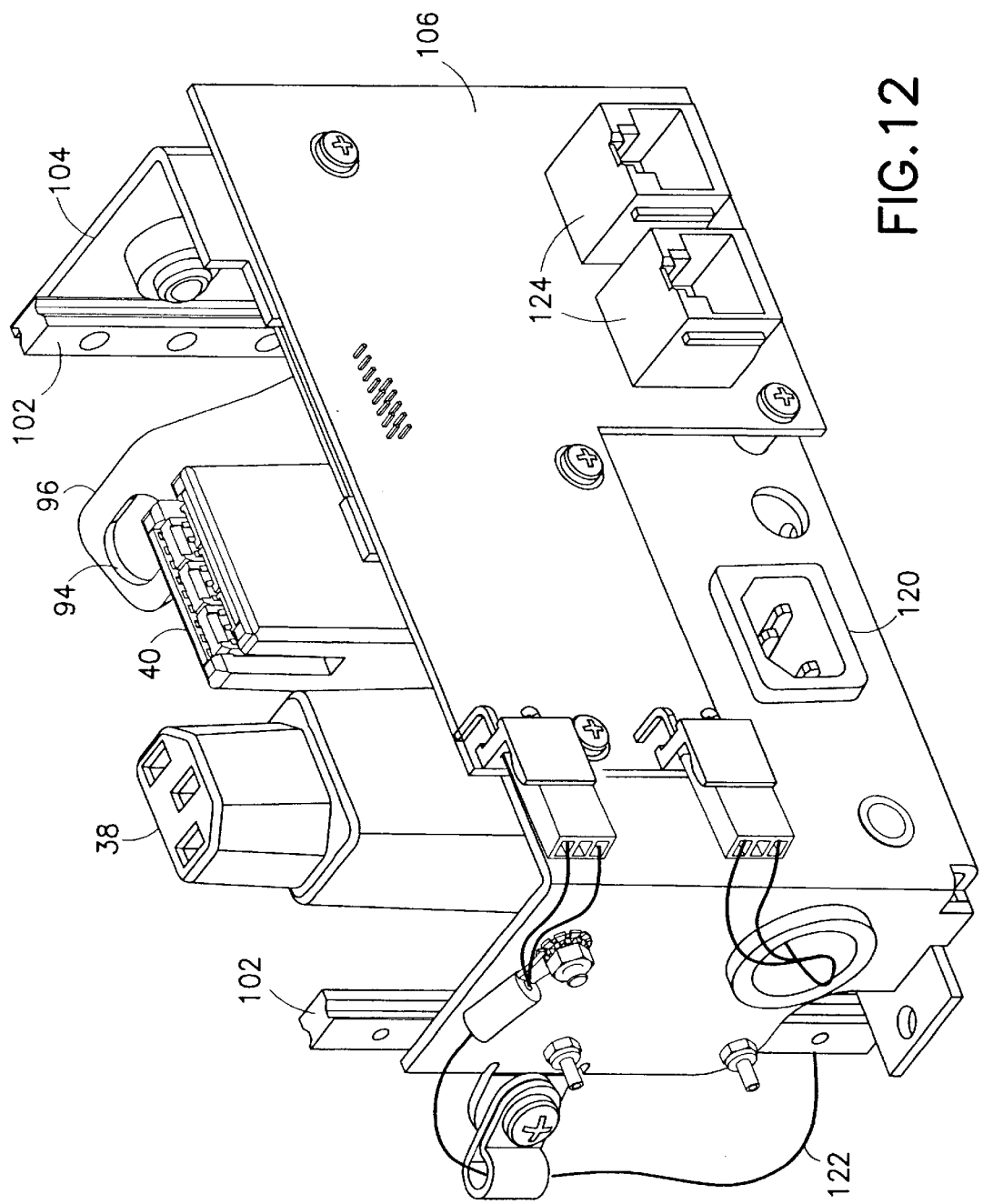
FIG. 12 is a drawing showing the electrical connector subassembly of the docking station in accordance with the preferred embodiment of the invention, viewed from behind.

The connector assembly will now be described with reference to FIGS. 10–12. Referring to FIG. 10, the connector assembly comprises an AC power connector 38 and a communications connector 40 which are seated on a connector platform 98 which is vertically displaceable. The ends of the connector platform 98 have brackets which are attached to respective carriages 100 which slide on a pair of vertical rails 102. The rails are attached to a connector mounting bracket 104, which is in turn fastened to the bottom housing. A printed circuit board 106 is mounted to the back wall of the connector mounting bracket 104. The communications connection comprises an 18-pin flexible printed circuit board 108 which is anchored at the back wall of the connector mounting bracket 104. The flexible printed circuit board 108 flexes to maintain the connection between the back wall/PCB and the communications connector 40 as the latter moves up and down with the displaceable connector platform 98. Similarly, the AC power connector 38 is electrically coupled to a power inlet 120 at the back of the connector assembly, seen in FIG. 12, via an AC power cable 122. Preferably, the AC power cable 122 comprises highly flexible high-voltage wires covered by a flexible braided nylon tube-type sheath which flexes and forms a rolling "C" shape as the connector platform 98 moves up and down. The AC power inlet 120 connects to an external AC power source. Numerals 124 are RJ45 connectors which attach to the back of the printed circuit board 106.

As seen in FIG. 10, the connector platform 98 has an extended tab 110 which carries a pin 112. The pin 112 extends through an arcuate slot 114 formed in the member of L-shaped connector lever 96 which is shown in a generally horizontal position in FIGS. 10 and 11. In addition, as best seen in FIG. 11, the connector mounting bracket 104 has an extended tab 116 which carries a pivot pin 118. The pivot pin 118 is coupled to the corner of the L-shaped connector lever 96. The connector lever 96 is pivotable about pivot pin 118 in a counterclockwise direction as seen in FIG. 10. As the connector lever 96 pivots, the arcuate slot 114 rotates about the axis of the pivot pin 118 along an upward arc. The pin 112, which rides in slot 114 and is connected to the connector platform 98, is restrained from moving in any direction other than vertical. As the slot 114 rotates counterclockwise along an arc, the pin 112 (and platform 98 connected thereto) is pushed upward by and slides along the lower edge of the slot 114. As a result, the counterclockwise rotation of the connector lever 96 is converted into upward vertical displacement of the connector platform 98 and connectors 38 and 40 thereon. That counterclockwise rotation of the connector lever 96 is, in turn, the result of the operator pushing the user lever from its halfway position to its leftmost position.

To reverse all of the above-described mechanical actions, the operator simply pushes the user lever from its leftmost to its rightmost position, and then lifts the patient monitor, causing the plunger pin 30 to spring upward. When the large-diameter section of the plunger pin 30 enters and stays in the keyhole 50, the docking station is cocked and ready to receive the next patient monitor.

Although the preferred embodiments have been disclosed in the context of docking portable patient monitors, it should be appreciated that the docking station of the present invention is not limited in its application to docking of patient monitors. For example, a station may be designed for docking other types of portable electronic devices, e.g., portable electronic devices having application outside of the health care industry, such as laptop or hand-held computers.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A docking station for a portable electronic device comprising:
    a housing comprising a support surface;
    a plunger penetrating said housing;
    a lever which is movable between first and second positions and which is operatively coupled to said plunger; and
    an extension spring having one end operatively coupled to said lever and another end which is fixed inside said housing, said spring urging said member from said first position toward said second position,
    wherein said lever is locked in said first position when said plunger is in an up position and is free to move toward said second position under the influence of said extension spring when said plunger is in a down position.

2. The docking station as recited in claim 1, further comprising a mounting bracket attached to said housing, said another end of said extension spring being fixed to said mounting bracket.

3. The docking station as recited in claim 2, wherein said main lever is pivotably mounted to said mounting bracket, further comprising a clamp which is pivotably coupled to said mounting bracket and linked to said main lever, said clamp moving from a retracted position to an extended position as said main lever pivots from said first position to said second position.

4. The docking station as recited in claim 1, further comprising:
    a cylindrical structure for said plunger having one end at least partially closed; and
    a compression spring seated inside said cylindrical structure between said plunger and said at least partially closed end.

5. The docking station as recited in claim 1, further comprising a clamp which is coupled to said main lever, said clamp moving from a retracted position to an extended position as said main lever moves from said first position to said second position.

6. The docking station as recited in claim 1, wherein said main lever comprises an arcuate slot which communicates with a keyhole, said arcuate slot having a width less than a diameter of said keyhole, and said plunger comprises coaxial first and second circular cylindrical portions, said first circular cylindrical portion having a diameter slightly less than said width of said arcuate slot and said second circular cylindrical having a diameter greater than said width of said slot and slightly less than said diameter of said keyhole.

7. The docking station as recited in claim 1, further comprising:
    a platform which is vertically translatable inside said housing;
    an electrical connector mounted to said platform; and
    a mechanical subassembly for converting motion of said main lever from said second position to a third position into upward vertical translation of said platform from a first elevation to a second elevation,
    wherein said housing comprises an opening, and said electrical connector protrudes through said opening and outside said housing when said platform is at said second elevation.

8. The docking station as recited in claim 7, wherein said housing comprises an AC power inlet, and said electrical connector is electrically coupled to said AC power inlet.

9. The docking station as recited in claim 8, further comprising a flexible cable for electrically coupling said electrical connector to said AC power inlet.

10. The docking station as recited in claim 7, wherein said housing comprises a communications interface, and said electrical connector is electrically coupled to said communications interface.

11. The docking station as recited in claim 10, further comprising a flexible printed circuit for electrically coupling said electrical connector to said communications interface.

12. The docking station as recited in claim 7, further comprising:
    first and second rails which are mutually parallel and aligned vertically; and
    first and second carriages which ride on and translate along said first and second rails respectively,
    wherein said platform is attached to said first and second carriages.

13. The docking station as recited in claim 7, wherein said main lever is pivotable about a first pivot axis, and said mechanical subassembly comprises an intermediate lever which is pivotable about a second pivot axis, said intermediate lever having a first slot with a radius of curvature centered at said first pivot axis, further comprising a first pin attached to said main lever which penetrates said first slot.

14. The docking station as recited in claim 13, wherein said first slot has a length which allows said first pin to travel the length of said first slot during pivoting of said main lever from said first position to said second position, said intermediate lever being pivoted by engagement of said first pin with the end of said first slot as said main lever pivots from said second position to said third position.

15. The docking station as recited in claim 14, further comprising a connector lever which couples said platform to said intermediate lever, said connector lever being pivotable about a third axis which is generally perpendicular to said second pivot axis.

16. The docking station as recited in claim 15, wherein said connector lever comprises second and third slots, further comprising a second pin attached to said intermediate lever which penetrates said second slot, and a third pin attached to said platform which penetrates said third slot.

17. The docking station as recited in claim 7 wherein said main lever comprises a camming slot and further comprising:
    a door which is slidable between open and closed positions, said opening in said housing being closed by said door when said door is in said closed position and being open when said door is in said open position; and
    a cam follower connected to said door, said cam follower comprising a pin which penetrates that camming slot,
    wherein said cam follower acts to move said door from said closed position to said open position as said main lever moves from said first position to said second position.

18. A docking station for an electronic device, comprising:
- a housing comprising a support surface for supporting an electronic device;
- a lever which is pivotable about a fixed pivot point located inside said housing, said lever having a free end protruding out of said housing; and
- first and second clamps which are coupled to said lever, said first and second clamps pivoting from respective retracted positions, whereat an electronic device is not clamped in place, to respective extended positions, whereat an electronic device is clamped in place, as said lever is pivoted from a first position to a second position.

19. The docking station as recited in claim 18, further comprising a mounting bracket attached to said housing, said lever and said first and second clamps being pivotably coupled to said mounting bracket.

20. The docking station as recited in claim 18, further comprising first and second lever rods for respectively coupling said first and second clamps to said lever.

21. A docking station for an electronic device, comprising:
- a housing comprising a support surface for supporting an electronic device;
- a main lever which is pivotable about a fixed pivot point located inside said housing;
- a platform which translateable only vertically inside said housing;
- an electrical connector mounted to said platform; and
- a mechanical subassembly for converting pivoting of said main lever into upward vertical displacement of said platform,
- wherein said housing comprises an opening, and said electrical connector protrudes through said opening and outside said housing when said platform is translated vertically upward from a first elevation corresponding to a first position of said main lever to a second elevation corresponding to a second position of said main lever.

22. The docking station as recited in claim 21, wherein said housing comprises an AC power inlet, and said electrical connector is electrically coupled to said AC power inlet.

23. The docking station as recited in claim 22, further comprising a flexible cable for electrically coupling said electrical connector to said AC power inlet.

24. The docking station as recited in claim 21, wherein said housing comprises a communications interface, and said electrical connector is electrically coupled to said communications interface.

25. The docking station as recited in claim 24, further comprising a flexible printed circuit for electrically coupling said electrical connector to said communications interface.

26. The docking station as recited in claim 22, further comprising:
- first and second rails which are mutually parallel and aligned vertically; and
- first and second carriages which ride on and translate along said first and second rails respectively,
- wherein said platform is attached to said first and second carriages.

27. The docking station as recited in claim 21, wherein said mechanical subassembly comprises an intermediate lever which is pivotable, said intermediate lever having a first slot with a radius of curvature centered at a pivot axis of said main lever, further comprising a first pin attached to said main lever which penetrates said first slot.

28. The docking station as recited in claim 27, wherein said first slot has a length which allows said first pin to travel the length of said first slot during pivoting of said main lever from said first position to said second position, said intermediate lever being pivoted by engagement of said first pin with the end of said first slot as said main lever pivots from said second position to said third position.

29. The docking station as recited in claim 28, further comprising a connector lever which couples said platform to said intermediate lever, said connector lever being pivotable about a pivot axis which is generally perpendicular to a pivot axis of said intermediate lever.

30. The docking station as recited in claim 29, wherein said connector lever comprises second and third slots, further comprising a second pin attached to said intermediate lever which penetrates said second slot, and a third pin attached to said platform which penetrates said third slot.

31. A docking station for an electronic device, comprising: a housing for supporting the electronic device in a predetermined position; a release mechanism which is activated by the weight of the electronic device in said predetermined position; and a spring-loaded clamping mechanism held in a non-clamping state prior to said release mechanism being activated and changed to a clamping state under the influence of said spring loading in response to activation of said release mechanism, wherein the electronic device is clamped by said clamping mechanism in said clamping state.

32. The docking station as recited in claim 31, wherein said release mechanism comprises a plunger which penetrates an opening in said housing and which is displaced downward and further into said housing as the electronic device is lowered into said predetermined position plunger which penetrates an opening in said housing.

33. A docking station for an electronic device, comprising: a housing for supporting the electronic device in a predetermined position; a platform which is translatable only vertically inside said housing; an electrical connector mounted to said platform; and a lever assembly coupled to said platform and comprising a user-operable device protruding external to said housing, wherein said platform is translated upward in response to a predetermined movement of said user-operable device, whereby said electrical connector is mated with an electrical connector of the electronic device.

34. The docking station as recited in claim 33, wherein said user-operable device comprises a lever which is pivotable relative to said housing.

* * * * *